US009457193B2

(12) United States Patent
Klimovitch et al.

(10) Patent No.: US 9,457,193 B2
(45) Date of Patent: Oct. 4, 2016

(54) DUAL CHAMBER LEADLESS PACEMAKER PROGRAMMER AND METHOD

(71) Applicant: Pacesetter, Inc., Sunnyvale, CA (US)

(72) Inventors: Gleb Klimovitch, Santa Clara, CA (US); Timothy Edward Ciciarelli, San Jose, CA (US); Benjamin T. Persson, Sunnyvale, CA (US)

(73) Assignee: Paceseter, Inc., Sunnyvale, CA (US)

( * ) Notice: Subject to any disclaimer, the term of this patent is extended or adjusted under 35 U.S.C. 154(b) by 0 days.

(21) Appl. No.: 14/931,118

(22) Filed: Nov. 3, 2015

(65) Prior Publication Data

US 2016/0121127 A1    May 5, 2016

Related U.S. Application Data

(60) Provisional application No. 62/084,476, filed on Nov. 25, 2014, provisional application No. 62/074,541, filed on Nov. 3, 2014.

(51) Int. Cl.
| | |
|---|---|
| *A61N 1/372* | (2006.01) |
| *A61N 1/362* | (2006.01) |
| *A61N 1/375* | (2006.01) |
| *H04W 52/04* | (2009.01) |
| *H04W 56/00* | (2009.01) |
| *A61N 1/365* | (2006.01) |
| *A61N 1/37* | (2006.01) |

(52) U.S. Cl.
CPC ......... *A61N 1/37288* (2013.01); *A61N 1/3622* (2013.01); *A61N 1/3756* (2013.01); *A61N 1/37235* (2013.01); *H04W 52/04* (2013.01); *H04W 56/001* (2013.01); *A61N 1/36514* (2013.01); *A61N 1/3702* (2013.01); *A61N 1/37217* (2013.01)

(58) Field of Classification Search
None
See application file for complete search history.

(56) References Cited

U.S. PATENT DOCUMENTS

| | | | | |
|---|---|---|---|---|
| 6,141,588 | A * | 10/2000 | Cox | A61N 1/3622 128/903 |
| 7,565,195 | B1 * | 7/2009 | Kroll | A61N 1/37288 607/2 |
| 8,019,419 | B1 * | 9/2011 | Panescu | A61N 1/05 607/33 |
| 8,457,742 | B2 * | 6/2013 | Jacobson | A61N 1/3621 607/2 |
| 2011/0160801 | A1 * | 6/2011 | Markowitz | A61B 5/0028 607/60 |
| 2012/0109236 | A1 * | 5/2012 | Jacobson | A61N 1/368 607/4 |

* cited by examiner

Primary Examiner — Brian T Gedeon
(74) Attorney, Agent, or Firm — Theresa A. Raymer

(57) ABSTRACT

Systems and methods for providing communications between an external device and first and second leadless pacemakers (LPs) located in a heart are provided. A method includes receiving first and second event messages from the first and second LPs, the first and second event messages received at different points in time at the external device, determining the signal strengths of the first and second event messages, respectively, as received at the external device, adjusting first and second LP discrimination thresholds based on the received signal strengths of the first and second event messages, respectively, and utilizing the first and second LP discrimination thresholds to identify which of the first and second LP transmits subsequent event messages, in order for the external device to independently communicate with the first and second LPs.

17 Claims, 11 Drawing Sheets

DUAL CHAMBER LEADLESS PACEMAKER PROGRAMMER AND METHOD

CROSS REFERENCE TO RELATED APPLICATIONS

This application claims the benefit of U.S. Provisional Application No. 62/084,476, entitled IMPLANTABLE DEVICE INTRA-CARDIAC COMMUNICATIONS SYSTEM AND METHOD, filed Nov. 25, 2014. This application also claims the benefit of U.S. Provisional Application No. 62/074,541, entitled IMPLANTABLE DEVICE INTRA-CARDIAC COMMUNICATIONS SYSTEM AND METHOD, filed Nov. 3, 2014. Each patent application identified above is incorporated herein by reference in its entirety to provide continuity of disclosure.

FIELD OF THE INVENTION

The invention relates to the field of implantable cardiac stimulation devices and specifically to a programmer that supports a multichambered leadless pacemaker system.

BACKGROUND OF THE INVENTION

Currently, implantable medical devices (IMDs) utilize one or more electrically-conductive leads (which traverse blood vessels and heart chambers) in order to connect a canister with electronics and a power source (the can) to electrodes affixed to the heart for the purpose of electrically exciting cardiac tissue (pacing) and measuring myocardial electrical activity (sensing). These leads may experience certain limitations, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction. Further, conventional pacemakers with left ventricle (LV) pacing/sensing capability require multiple leads and a complex header on the pacemaker.

A small sized IMD has been proposed that mitigates the aforementioned complications, termed a leadless pacemaker (LP) that is characterized by the following features: electrodes are affixed directly to the "can" of the device; the entire device is attached to or within the heart; and the LP is capable of pacing and sensing in the chamber of the heart where it is implanted.

The LPs that have been proposed thus far offer limited functional capability. The LP is able to sense in one chamber and deliver pacing pulses in that same chamber, and thus offer single chamber functionality. For example, an LP device that is located in the right atrium would be limited to offering AAI mode functionality. An AAI mode LP can only sense in the right atrium, pace in the right atrium and inhibit pacing function when an intrinsic event is detected in the right atrium within a preset time limit. Similarly, an LP device that is located in the right ventricle would be limited to offering VVI mode functionality. A VVI mode LP can only sense in the right ventricle, pace in the right ventricle and inhibit pacing function when an intrinsic event is detected in the right ventricle within a preset time limit.

It has been proposed to implant sets of multiple LP devices within a single patient, such as one or more LP devices located in the right atrium and one or more LP devices located in the right ventricle. The atrial LP devices and the ventricular LP devices wirelessly communicate with one another to convey pacing and sensing information therebetween to coordinate pacing and sensing operations between the various LP devices. There remains a need for a programmer that supports such a multi chambered leadless pacemaker system.

SUMMARY

In one embodiment, the present disclosure is directed to a method for providing communications between an external device and first and second leadless pacemakers (LPs) located in a heart. The method includes receiving first and second event messages from the first and second LPs, the first and second event messages received at different points in time at the external device, determining the signal strengths of the first and second event messages, respectively, as received at the external device, adjusting first and second LP discrimination thresholds based on the received signal strengths of the first and second event messages, respectively, and utilizing the first and second LP discrimination thresholds to identify which of the first and second LP transmits subsequent event messages, in order for the external device to independently communicate with the first and second LPs.

In another embodiment, the present disclosure is directed to a programmer for use in a cardiac stimulation system is provided. The programmer includes a memory device, and a processor coupled to the memory device, the processor configured to receive first and second event messages from first and second leadless pacemakers (LPs) located in a heart, the first and second event messages received at different points in time at the programmer, determine the signal strengths of the first and second event messages, respectively, as received at the programmer, adjust first and second LP discrimination thresholds based on the received signal strengths of the first and second event messages, respectively, and utilize the first and second LP discrimination thresholds to identify which of the first and second LP transmits subsequent event messages, in order for the programmer to independently communicate with the first and second LPs.

In another embodiment, the present disclosure is directed to a system for applying cardiac stimulation to a patient. The system includes a first leadless pacemaker (LP) implanted in a first chamber of a heart of the patient, a second LP implanted in a second chamber of the heart, and a programmer configured to receive first and second event messages from the first and second leadless pacemakers LPs, the first and second event messages received at different points in time at the programmer, determine the signal strengths of the first and second event messages, respectively, as received at the programmer, adjust first and second LP discrimination thresholds based on the received signal strengths of the first and second event messages, respectively, and utilize the first and second LP discrimination thresholds to identify which of the first and second LP transmits subsequent event messages, in order for the programmer to independently communicate with the first and second LPs.

BRIEF DESCRIPTION OF THE DRAWINGS

Embodiments of the invention relating to both structure and method of operation may best be understood by referring to the following description and accompanying drawings, in which similar reference characters denote similar elements throughout the several views.

DETAILED DESCRIPTION

In some embodiments of an illustrative cardiac pacing system, one or more leadless cardiac pacemakers with low-power conducted communication can perform single-chamber pacing, dual-chamber pacing, CRT-D, or other pacing, and may or may not be co-implanted with an ICD.

Figure 1:
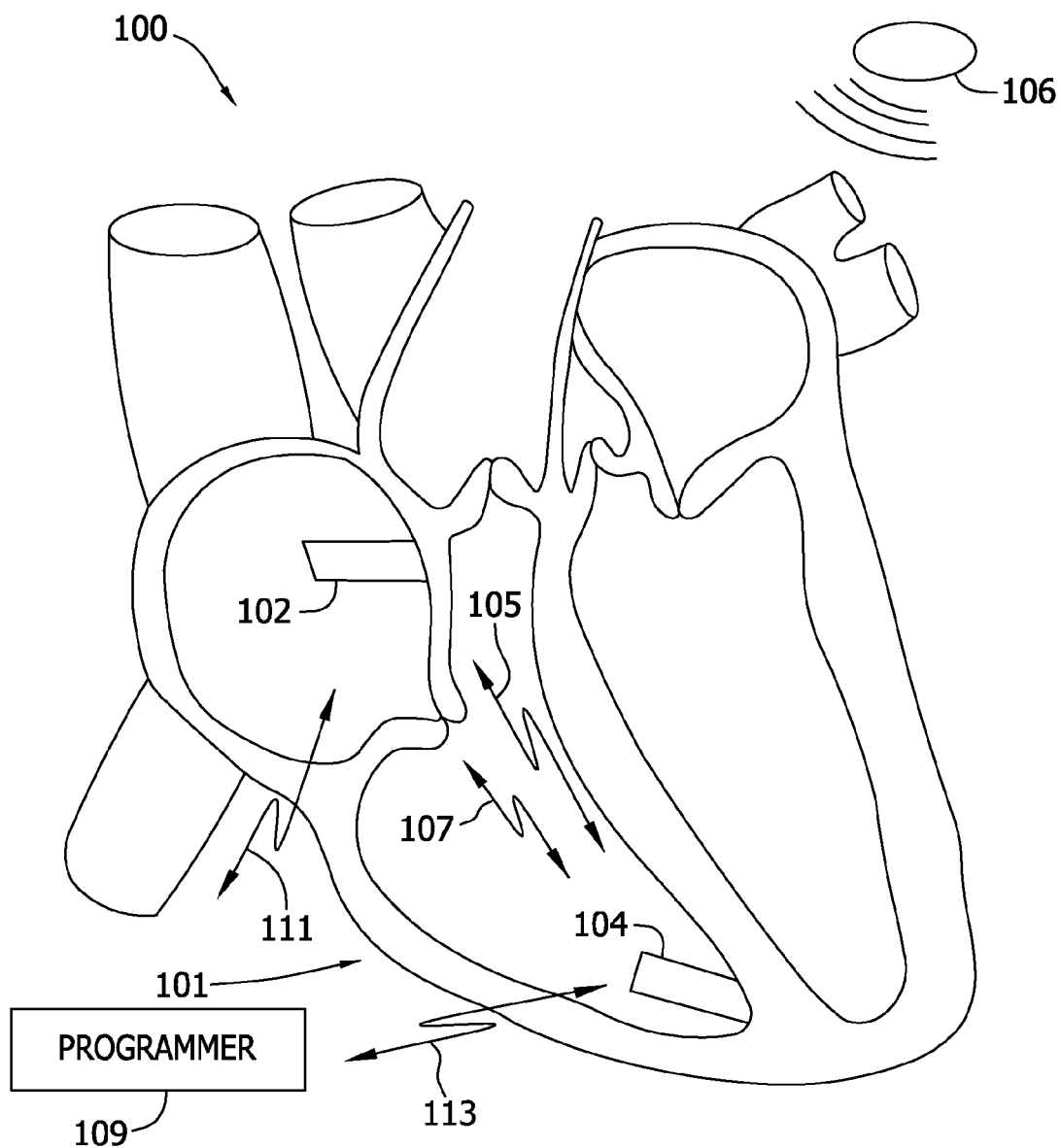
FIG. 1 illustrates a cardiac stimulation system in accordance with embodiments herein.

FIG. 1 illustrates a system 100 formed in accordance with embodiments herein as implanted in a heart 101. The system 100 comprises two or more leadless pacemakers (LPs) 102, 104 located in different chambers of the heart. LP 102 is located in a right atrium, while LP 104 is located in a right ventricle. LPs 102 and 104 communicate with one another to inform one another of various local physiologic activity such as local intrinsic events, local paced events and the like. LPs 102 and 104 may be constructed in a similar manner, but operate differently based upon which chamber LPs 102 and 104 are located. LPs 102 and 104 utilize two separate and distinct communications channels 105, 107 when communicating implant to implant ("i2i") that operate as explained herein to reduce power usage between and during implant event messages. External device (programmer) 109 may receive first and second event messages independently from LPs 102 and 104, at different points in time, through conductive communication at the external device (i.e., programmer 109) over a common physical channel.

In some embodiments, one or more leadless cardiac pacemakers 102, 104 can be co-implanted with the implantable cardioverter-defibrillator (ICD) 106. Each leadless cardiac pacemaker 102, 104 uses two or more electrodes located within, on, or within a few centimeters of the housing of the pacemaker, for pacing and sensing at the cardiac chamber, for bidirectional communication with one another, with the external programmer 109, and the ICD 106.

Figure 2:
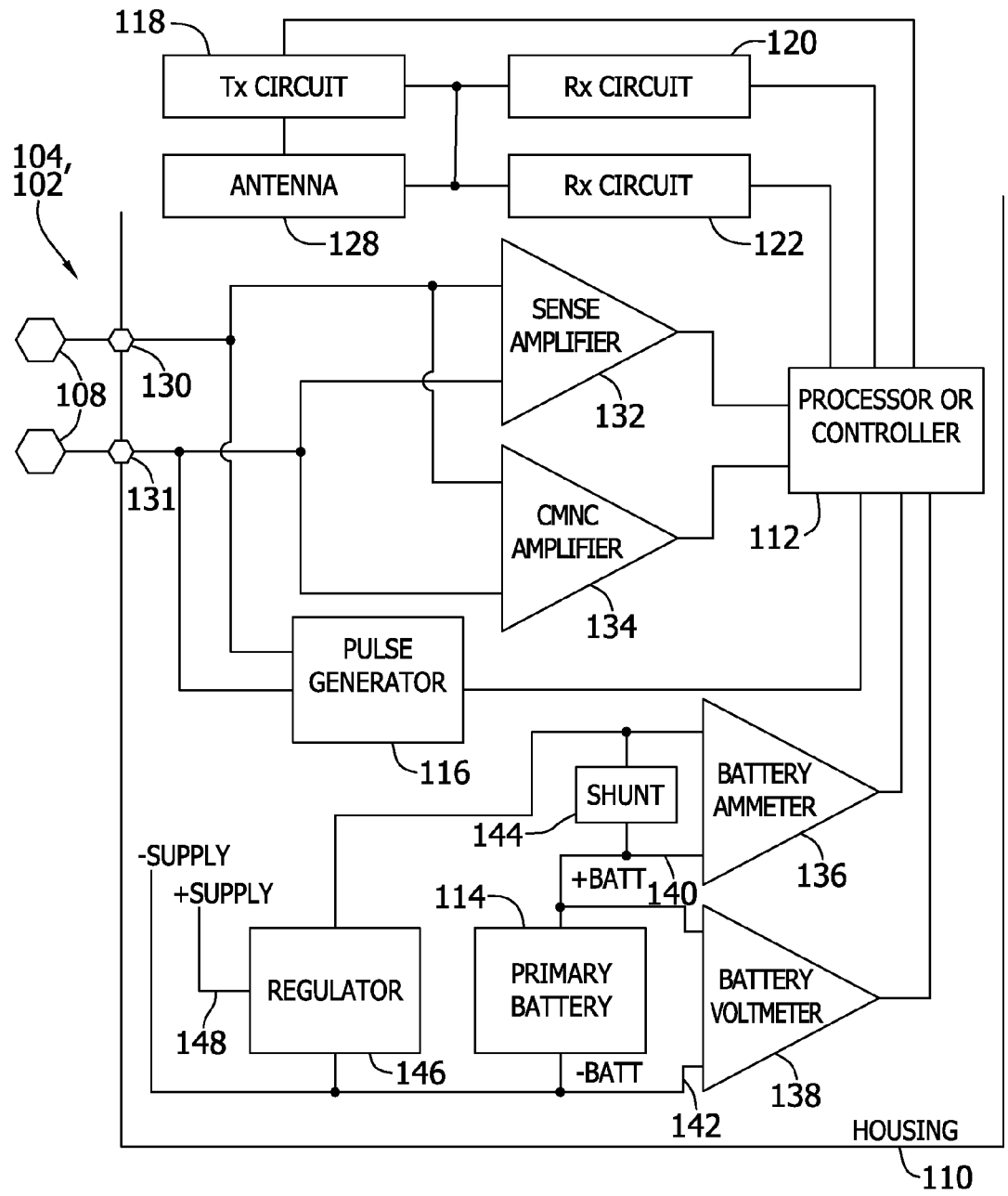
FIG. 2 illustrates a block diagram of a single LP in accordance with embodiments herein.

Referring to FIG. 2, a pictorial diagram shows an embodiment for portions of the electronics within LP 102, 104 configured to provide conducted communication through the sensing/pacing electrode. One or more of LPs 102 and 104 comprise at least two leadless electrodes 108 configured for delivering cardiac pacing pulses, sensing evoked and/or natural cardiac electrical signals, and uni-directional or bi-directional communication.

LP 102, 104 includes a transmitter 118 and first and second receivers 120, 122 that collectively define separate first and second communications channels 105 and 107 (FIG. 1) to convey LP wake up notices and event signaling, respectively, (among other things) between LPs 102 and 104. The transmitter 118 and receivers 120, 122 may each utilize a separate antenna or may utilize a common antenna 128. Optionally, LPs 102 and 104 communicate conductively over a common physical channel via the same electrodes 108 that are also used to deliver pacing pulses. Usage of the electrodes 108 for communication enables the one or more LP 102, 104 for antenna-less and telemetry coil-less communication.

When a leadless pacemaker senses an intrinsic event or delivers a paced event, the corresponding leadless pacemaker transmits an implant event message to the other leadless pacemaker. For example, when an atrial LP 102 senses/paces an atrial event, the atrial LP 102 transmits an implant event message, including an event marker indicative of a nature of the event (e.g., intrinsic/sensed atrial event, paced atrial event). When a ventricular LP 104 senses/paces a ventricular event, the ventricular LP 104 transmits an implant event message, including an event marker indicative of a nature of the event (e.g., intrinsic/sensed ventricular event, paced ventricular event). The implant event messages may be formatted in various manners.

In accordance with embodiments herein, external programmer 109 may communicate over a programmer-to-LP channel, with the LP 102, 104 utilizing the same event message scheme. External programmer 109 may listen to the event message transmitted between LPs 102 and 104 and synchronize programmer to implant communication such that the programmer 109 does not transmit communications signals 113 until after an implant to implant messaging sequence is completed.

FIG. 2 depicts a single LP 102, 104 and shows the LP's functional elements substantially enclosed in a hermetic housing 110. The LP 102, 104 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, circuits 134 for receiving information from at least one other device via the electrodes 108, and a pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

Additionally or alternatively, one or more leadless electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more leadless cardiac pacemakers 102, 104 and/or the ICD 106 and transmit data including designated codes for events detected or created by an individual pacemaker. Individual pacemakers can be configured to issue a unique code corresponding to an event type and a location of the sending pacemaker.

Information communicated on the incoming communication channel can include but is not limited to pacing rate, pulse duration, sensing threshold, and other parameters commonly programmed externally in conventional pacemakers. Information communicated on the outgoing communication channel can include but is not limited to programmable parameter settings, pacing and sensing event counts, battery voltage, battery current, device health, and other information commonly displayed by external programmers used with conventional pacemakers. The outgoing communication channel can also echo information from the incoming channel, to confirm correct programming.

For example, in some embodiments an individual LP 102 can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer 109. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to the leadless cardiac pacemakers 102, 104 configured for implantation in electrical contact with a cardiac chamber and for performing cardiac rhythm management functions in combination with the implantable ICD 106. The implantable ICD 106 and the one or more leadless cardiac pacemakers 102, 104 configured for leadless intercommunication by information conduction through body tissue and/or wireless transmission between transmitters and receivers in accordance with the discussed herein.

In a further embodiment, a cardiac pacing system 100 comprises at least one leadless cardiac pacemaker 102 configured for implantation in electrical contact with a cardiac chamber and configured to perform cardiac pacing functions in combination with the co-implanted implantable cardioverter-defibrillator (ICD) 106. The leadless cardiac pacemaker 102 or pacemakers 102 and 104 comprise at least two leadless electrodes 108 configured for delivering cardiac pacing pulses, sensing evoked and/or natural cardiac electrical signals, and transmitting information to the co-implanted ICD 106.

The LP 102, 104 can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. The LP 102, 104 receiving the communication decodes the information and responds depending on the location of the receiving pacemaker and predetermined system functionality.

Also shown in FIG. 2, the primary battery 114 has positive terminal 140 and negative terminal 142. A suitable primary battery has a volume less than 1 cubic centimeter, and a lifetime greater than 5 years (depending on the current draw). Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health. The illustrative power supply can be a primary battery 114. In various embodiments, the LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

Figure 3:
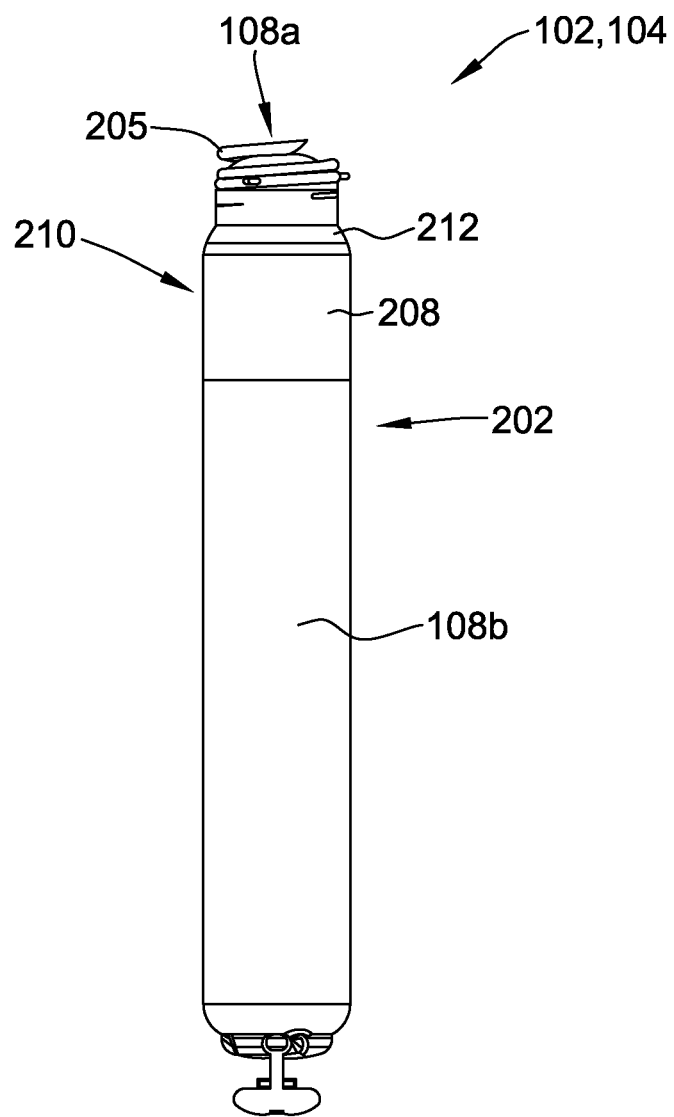
FIG. 3 illustrates a LP in accordance with embodiments herein.

FIG. 3 shows a LP 102, 104. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue.

The housing can also include an electronics compartment 210 within the housing that contains the electronic components necessary for operation of the pacemaker, including, for example, a pulse generator, communication electronics, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 3) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Figure 4:
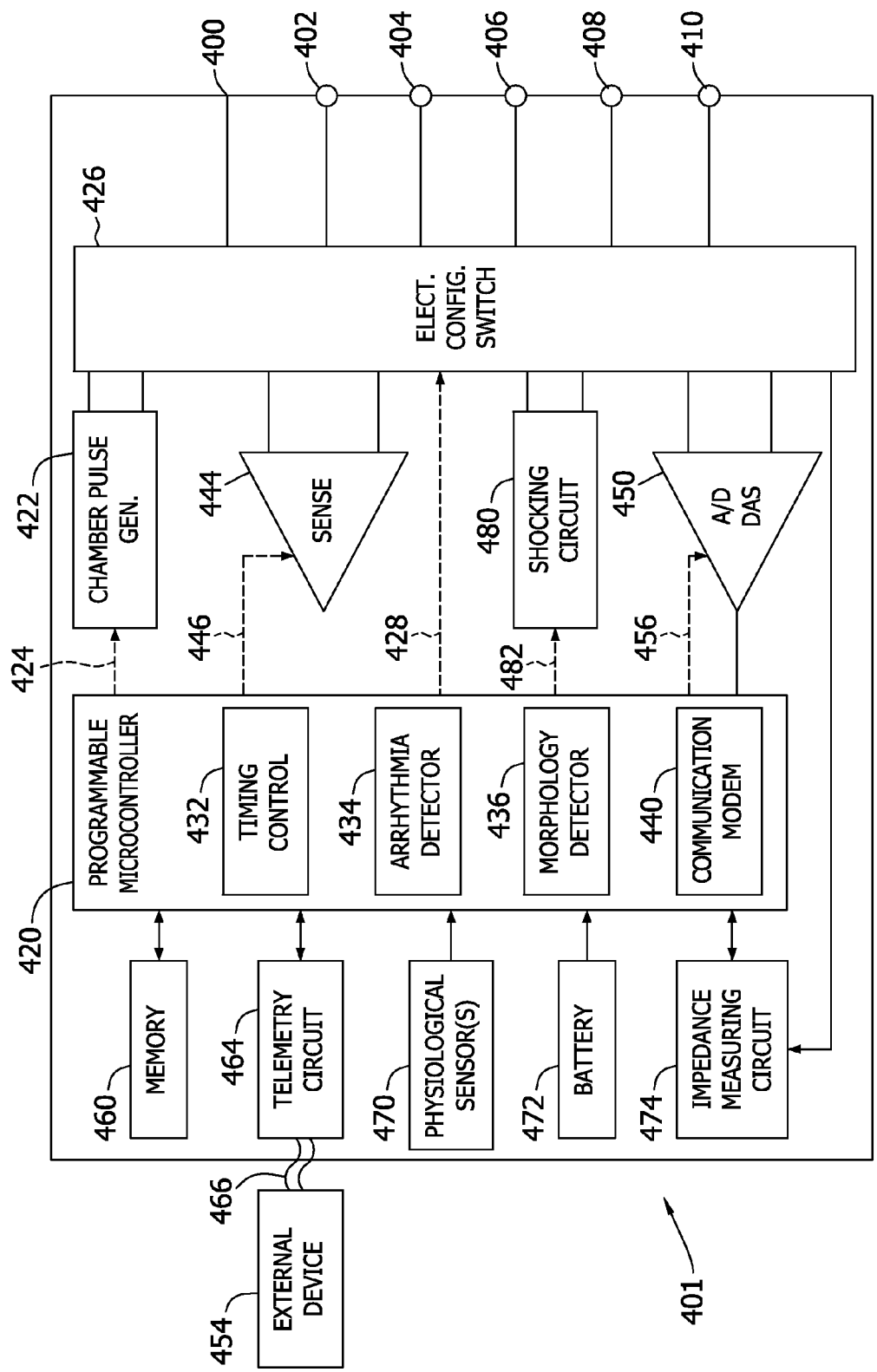
FIG. 4 illustrates a block diagram of an LP that is implanted into the patient in accordance with embodiments herein.

FIG. 4 shows a block diagram of an LP 401 that is implanted into the patient as part of the implantable cardiac system in accordance with embodiments herein. The LP 401 may be implemented as a full-function biventricular pacemaker, equipped with both atrial and ventricular sensing and pacing circuitry for four chamber sensing and stimulation therapy (including both pacing and shock treatment). Optionally, the LP 401 may provide full-function cardiac resynchronization therapy. Alternatively, the LP 401 may be implemented with a reduced set of functions and components. For instance, the IMD may be implemented without ventricular sensing and pacing.

The LP 401 has a housing 400 to hold the electronic/computing components. The housing 400 (which is often referred to as the "can", "case", "encasing", or "case electrode") may be programmably selected to act as the return electrode for certain stimulus modes. Housing 400 further includes a connector (not shown) with a plurality of terminals 402, 404, 406, 408, and 410. The terminals may be connected to electrodes that are located in various locations on the housing 400 or elsewhere within and about the heart. The LP 401 includes a programmable microcontroller 420 that controls various operations of the LP 401, including cardiac monitoring and stimulation therapy. Microcontroller 420 includes a microprocessor (or equivalent control circuitry), RAM and/or ROM memory, logic and timing circuitry, state machine circuitry, and I/O circuitry.

LP 401 further includes a first pulse generator 422 that generates stimulation pulses for delivery by one or more electrodes coupled thereto. The pulse generator 422 is controlled by the microcontroller 420 via control signal 424. The pulse generator 422 is coupled to the select electrode(s) via an electrode configuration switch 426, which includes multiple switches for connecting the desired electrodes to the appropriate I/O circuits, thereby facilitating electrode programmability. The switch 426 is controlled by a control signal 428 from the microcontroller 420.

In the example of FIG. 4, a single pulse generator 422 is illustrated. Optionally, the IMD may include multiple pulse generators, similar to pulse generator 422, where each pulse generator is coupled to one or more electrodes and controlled by the microcontroller 420 to deliver select stimulus pulse(s) to the corresponding one or more electrodes.

Microcontroller 420 is illustrated as including timing control circuitry 432 to control the timing of the stimulation pulses (e.g., pacing rate, atrio-ventricular (AV) delay, atrial interconduction (A-A) delay, or ventricular interconduction (V-V) delay, etc.). The timing control circuitry 432 may also be used for the timing of refractory periods, blanking intervals, noise detection windows, evoked response windows, alert intervals, marker channel timing, and so on. Microcontroller 420 also has an arrhythmia detector 434 for detecting arrhythmia conditions and a morphology detector 436. Although not shown, the microcontroller 420 may further include other dedicated circuitry and/or firmware/software components that assist in monitoring various conditions of the patient's heart and managing pacing therapies.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted.

Programmer—LP Communications

Figure 5:
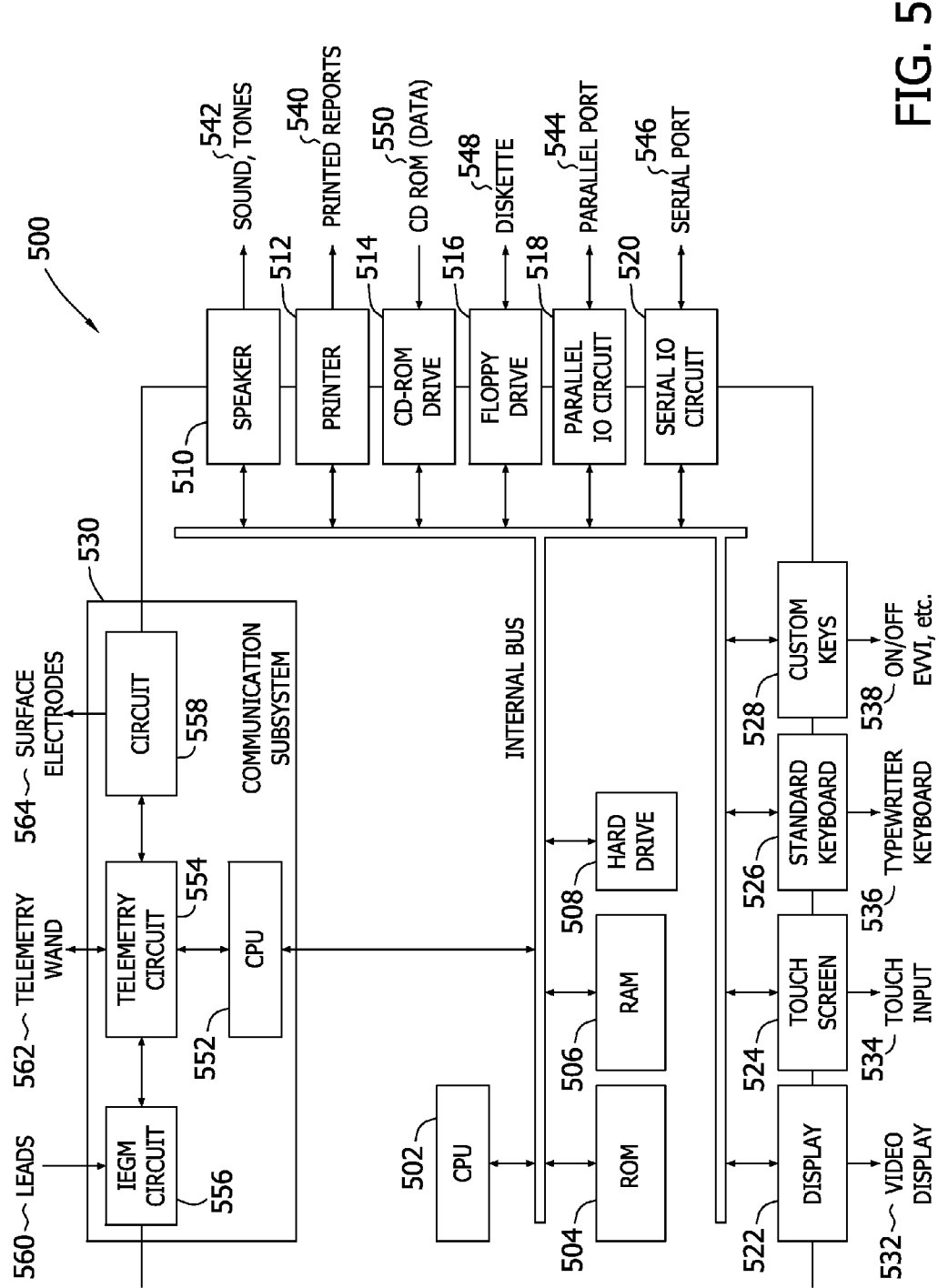
FIG. 5 illustrates a functional block diagram of an external device or programmer that is operated in accordance with the processes described herein to interface with LPs and IMDs as described herein in accordance with embodiments herein.

FIG. 5 illustrates a functional block diagram of an external device or programmer 500, such as programmer 109 (shown in FIG. 1) that is operated in accordance with the processes described herein to interface with LPs and IMDs as described herein. Programmer 500 may be a workstation, a portable computer, an LP/IMD programmer, a PDA, a cell phone and the like. Programmer 500 includes an internal bus that connects/interfaces with a Central Processing Unit (CPU) 502, ROM 504, RAM 506, a hard drive 508, a speaker 510, a printer 512, a CD-ROM drive 514, a floppy drive 516, a parallel I/O circuit 518, a serial I/O circuit 520, a display 522, a touch screen 524, a standard keyboard connection 526, custom keys 528, and a communications subsystem 530. The internal bus is an address/data bus that transfers information between the various components described herein. Hard drive 508 may store operational programs as well as data, such as waveform templates and detection thresholds.

CPU 502 typically includes a microprocessor, a microcontroller, or equivalent control circuitry, designed specifically to control interfacing with programmer 500 and with the LP/IMD. CPU 502 performs the chamber identification processes discussed above. CPU 502 may include RAM or ROM memory, logic and timing circuitry, state machine circuitry, and I/O circuitry to interface with the LP/IMD. Display 522 may be connected to a video display 532. Touch screen 524 may display graphic information relating to the LP/IMD. Display 522 displays various information related to the processes described herein. Touch screen 524 accepts a user's touch input 534 when selections are made. Keyboard 526 (e.g., a typewriter keyboard 536) allows the user to enter data to the displayed fields, as well as interface with communications subsystem 530. Furthermore, custom keys 528 turn on/off 538 (e.g., EVVI) programmer 500. Printer 512 prints copies of reports 540 for a physician to review or to be placed in a patient file, and speaker 510 provides an audible warning (e.g., sounds and tones 542) to the user. Parallel I/O circuit 518 interfaces with a parallel port 544. Serial I/O circuit 520 interfaces with a serial port 546. Floppy drive 516 accepts diskettes 548. Optionally, floppy drive 516 may include a USB port or other interface capable of communicating with a USB device such as a memory stick. CD-ROM drive 514 accepts CD ROMs 550.

Communications subsystem 530 includes a central processing unit (CPU) 552 in electrical communication with a telemetry circuit 554, which communicates with both an electrogram circuit 556 and a conductive communication circuit 558. Electrogram circuit 556 may be connected to implanted leads and/or surface ECG leads 560. Electrogram circuit 556 receives and processes IEGM and/or ECG signals as discussed herein. Optionally, the IEGM and/or ECG signals may be collected by the LP and/or IMD and then transmitted, to programmer 500, wirelessly to communications subsystem 530. Conductive communication circuit 558 provides conducted communications through one or more surface electrodes 564 that convey communications signals through the patient to the LPs and/or IMD (e.g. event messages, LP control commands, LP status request, etc.). The conductive communication circuit 558 also receives conducted communications (such as communications signals 111, 113 in FIG. 1), including event messages, from LP 102, 104 and/or ICD 106.

Communications subsystem 530 is configured to support communications with multiple LPs positioned in different chambers of the heart. Communications subsystem 530 communicates independently with the different LPs/ICDs.

Figure 6:
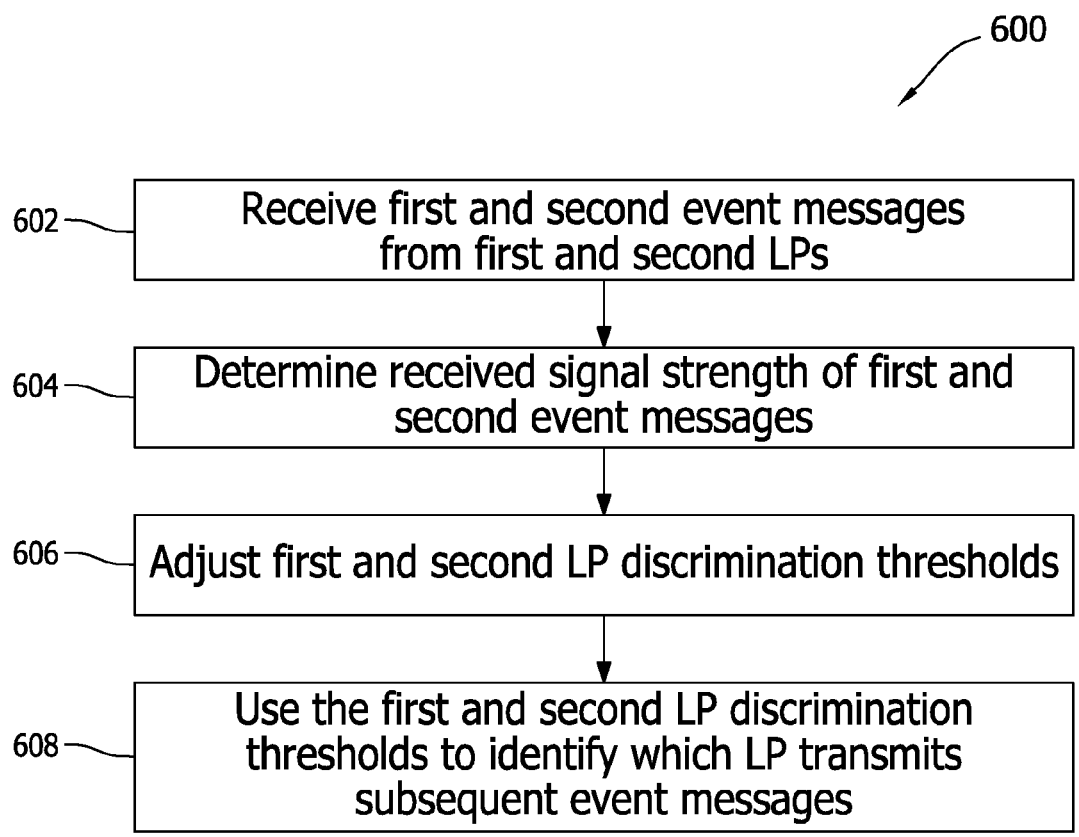
FIG. 6 illustrates a method for providing communication between an external device and LPs in accordance with the embodiments herein.

FIG. 6 is a flowchart of one embodiment of a method 600 for providing communications between an external device, such as programmer 109 (shown in FIG. 1) and/or programmer 500 (shown in FIG. 5), and first and second LPs located in the heart, such as LPs 102 and 104 (shown in FIG. 1). Method 600 includes receiving 602 first and second event messages from the first and second LPs, at different points in time, through conductive communication at the external device over a common physical channel. Method 600 further includes determining 604 received signal strengths of the first and second event messages, respectively, as received at the external device. Method 600 further includes adjusting 606 first and second LP discrimination thresholds based on the receive signal strengths of the first and second event messages, respectively. Method 600 further includes using 608 the first and second LP discrimination thresholds to identify which of the first and second LP transmits subsequent event messages, in order for the external device to independently communicate with the first and second LPs.

Returning to FIG. 1, for example, programmer 109 may communicate independently with two or more different LPs 102 and 104, as denoted by communications signals 111 and 113. Communication signals 111 and 113 that are transmitted and received by LPs 102 and 104 utilizing different signal strengths over the same physical channel. For example, programmer 109 may receive event messages within communications signal 111 from LP 102 at a first signal strength, while receiving event messages within communications signal 113 from LP 104 at a second signal strength that is lower than the first signal strength. Differences in the signal strength are based in part on attenuation of communication signals 111, 113 while propagating through the anatomy. The signal strengths at which programmer 109 receives event messages is dependent in part upon the distance between LPs 102 and 104 and programmer 109, the intervening anatomy and other factors that may introduce attenuation into communications signals 111, 113. Additionally or alternatively, differences in the signal strength may be based in part upon differences in the transmit power utilized at LPs 102 and 104. For example, LP 102 may be directed to transmit event messages at a lower power, relative to the event message transmit power utilized by LP 104.

Programmer 109 is configured to differentiate, without user intervention, between a patient with a single implant and a patient with multiple implants. Programmer 109 may communicate independently with the LPs based on various protocols. For example, communications subsystem 530 may utilize multiple/dual synchronization thresholds. For example, when communicating with two LPs 102 and 104, communications subsystem 530 may maintain a synchronization amplitude threshold for all incoming event messages. Communications subsystem 530 compares each potential incoming communication to the synchronization amplitude threshold and ignores or disregards the incoming communication when the incoming communication does not exceed the synchronization amplitude thresholds. When an incoming communications signal is received that exceeds the synchronization amplitude threshold, the signal is detected as a valid communication.

Figure 7:
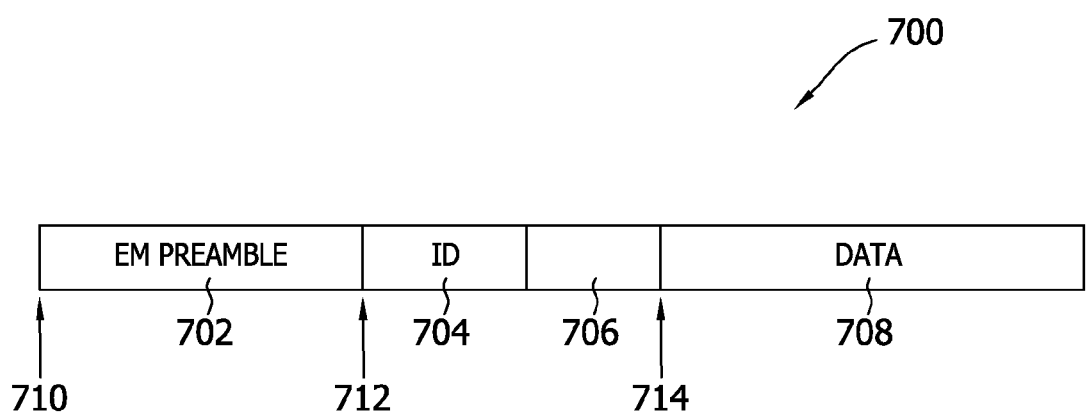
FIG. 7 illustrates an event message in accordance with the embodiments herein.

FIG. 7 illustrates an example of an event message 700, such as an i2i event message, formed in accordance with embodiments herein. Event message 700 includes an event message (EM) preamble field 702, a device ID field 704, a data protection field 706, and a data field 708. Optionally, additional fields may be provided between or after fields 702-708, or one or more of fields 702-708 may be omitted.

Device ID field 704 includes a bit pattern defining a device ID, such as indicating a chamber in which the device is located (e.g., right atrium (RA), right ventricle (RV), left atrium (LA), left ventricle (LV)). Data field 708 is used to convey various data between LPs 102 and 104 and to/from programmer 109. For example, data field 708 may include the event markers designating events sensed or paced at the corresponding LP. Optionally, data field 708 may be omitted entirely, and the event markers embedded into one or more of fields 702-708 may be omitted.

EM preamble field 702 includes a predefined bit pattern (also referred to as an event message identification (EMI) preamble) indicative of event message 700. LP 102, 104 and programmer 109 monitor one or more corresponding receive channels for event messages 700 (corresponding to or forming part of communications signals 105, 107, 111, 113). When LP 102, 104 or programmer 109 detects incoming signals, over a corresponding receive channel, and the incoming signal has an amplitude at 710 that crosses/exceeds the synchronization threshold, the incoming signal potentially representing event message 700 (e.g., an i2i communication). LP 102, 104 or programmer 109 analyzes the portion of event message 700 between 710 and 712, corresponding to EM preamble field 702 in search of a known EMI preamble. The EMI preamble may represent a common pattern for all implantable devices, or alternatively, unique EMI preambles may be designated for LPs in different chambers of the heart. For example, a ventricular LP may be assigned an EMI preamble of 0xAA, where the "AA" corresponds to a predefined bit pattern of "1010 1010". For example, an atrial LP may be assigned an EMI preamble of 0xD5, where the "D5" corresponds to a predefined bit pattern of "1101 0101".

LP 102, 104 or programmer 109 may use a preamble rejection threshold. For example, the LP or programmer may set a minimum acceptable difference between the minimum number of known "1" in detected EM preamble field 702 and the maximum number of known "0" in detected EM preamble field 702. LP 102, 104 or programmer 109 analyzes the incoming signal to determine a number of bits between points 710 and 712 that match a known EMI preamble. When the number of bits in EM preamble field 702 that match a known EMI preamble exceeds the preamble rejection threshold, LP 102, 104 or programmer 109 declares the incoming signal to correspond to an event message 700 to be further analyzed. Alternatively, when the number of bits in EM preamble field 702 that match a known EMI preamble falls below the preamble rejection threshold, LP 102, 104 or programmer 109 ignores or rejects the incoming signal as noise.

Programmer 109 searches all incoming communications signals that exceed the minimum amplitude synchronization threshold for the known configuration of "1s" and "0s" associated with a valid/known threshold setting preamble (EMI preamble). When a threshold setting preamble is identified, the amplitude of the communications signal is used to adjust the synchronization threshold associated with the LP (as shown in FIG. 6).

In accordance with some embodiments, LP 102, 104 and programmer 109 may continuously adjust (e.g., raise and lower) the synchronization threshold to be crossed before a potential/candidate event message 700 is identified at 710. For example, LP 102, 104 and programmer 109 may repeatedly decrease the synchronization threshold when no messages 700 are identified for a predetermined period of time. For example, LP 102, 104 and programmer 109 may utilize a synchronization rejection timer that provides an upper limit for an amount of time in which at least one event message 700 should be identified. When no incoming signals are identified to have sufficient amplitude to correspond to an event message 700 within the predetermined period of time, the synchronization rejection timer may time out. When the synchronization rejection timer times out, LP 102, 104 or programmer 109 may decrease the synchronization threshold to become more sensitive to lower amplitude incoming signals.

As another example, LP 102, 104 and programmer 109 may repeatedly increase the synchronization threshold when event messages 700 are identified to have sufficient amplitude at 710, but are rejected based upon invalid EMI preambles when EM preamble field 702 is analyzed. LP 102, 104 and programmer 109 may also maintain a count of a number of potential/candidate event messages 700 that are rejected. When the count of rejected potential event messages 700 exceed a rejection cluster threshold, LP 102, 104 and programmer 109 may lower the synchronization threshold.

As another example, LP 102, 104 and programmer 109 may increase the synchronization threshold when event messages 800 are received and identified to have relatively strong data signals, such as compared to other incoming signals, prior event messages 700, predetermined thresholds and the like.

In some embodiments, event message 700 may be formatted in various manners. For example, the event message 700 may include a designated marker field within the data field 708, where the designated marker field includes event markers encoded as bit patterns, as explained herein. Additionally or alternatively, LP 102, 104 may encode event markers in EM preamble field 702 of event message 700. For example, a ventricular LP may use 0xAA as an event marker in the EM preamble field, while an atrial LP may use xD5 as an event marker in the EM preamble field.

Additionally or alternatively, codes may be provided in EM preamble field 702 to differentiate between configurations. For example, a first EMI preamble code may indicate that the LP is configured to operation as a stand-alone single LP, while a second EMI preamble code may be used to indicate that the LP is configured to operate in combination with one or more other LPs. Once the different EMI preamble codes are identified by the programmer 109, processing proceeds as described herein.

In some embodiments, the event markers corresponding to sensed and paced events may be encoded within EM preamble field 702. Encoding the event markers in EM preamble field 702 affords the advantage of saving marker data bits at the expense of effectively shortening the portion of EM preamble field 702 that is available for synchronization. When a portion of EM preamble field 702 is used as the event marker, an available length for the threshold setting is shortened as the threshold setting preamble has a limited length, a portion of which is used as the predefined set of "1s" and "0s" for the programmer to set the threshold. When a portion of the preamble is used for other purposes, namely not explicitly defined for threshold setting, some of the threshold setting ability is lost, but with the possible benefit of more efficient communication. By encoding the LP device ID in the EMI preamble, the protocol affords the advantage that LPs 102 and 104 and programmer 109 do not rely on data decoding, but instead only utilize preamble decoding (pattern recognition) and preamble score rejection criteria.

In this embodiment, LPs 102 and 104 encode identification data in the event messages within each communications signal, where the identification data indicates the source LP from which the transmission originated (atrium or ventricle) and that it is part of a dual chamber system. Programmer 109 reads the identification data from each event message 700 to identify the source LP. Programmer 109 responds by adjusting the synchronization threshold associated with associated LP 102, 104. In this embodiment, the synchronization threshold is adjusted in proportion to the signal strength of the communications signal 111, 113 from LP 102, 104 for which communication is established, in order to provide a more reliable communication link. Programmer 109 repeats the foregoing threshold adjustment in connection with each separate LP. For example, when programmer 109 receives an event message over communications signal 111 from LP 102, programmer 109 assigns a first synchronization threshold to LP 102.

Separately, upon receiving an event message over communications signal 113 from LP 104, programmer 109 assigns a separate second synchronization threshold to LP 104. In this manner, when communications signals 111 and 113 are attenuated to different degrees due to anatomy or otherwise, programmer 109 remains able to establish communication with LP 102, 104. Optionally, throughout operation, programmer 109 may adjust the synchronization thresholds to values appropriate to signal strengths of the incoming communication signals 111, 113. In this way, the LP to programmer communication may be optimized for reliability for each implant, rather than the "stronger" implant being lowered to the same communication reliability level as the "weaker" implant, or the weaker implant being swamped by the stronger implant signal.

CPU 552 of communication subsystem 530 may identify individual LP 102, 104 in various manners. For example, digital identification (ID) data may be encoded in preamble 702 or another field of a known packet of event message 700. For example, the digital ID data may be encoded in a "sniffer" packet, when a protocol is utilized that includes sniffer packets. CPU 552 performs, under the control of software, packet analysis of event messages 700 that are classified as valid communications signals (based on the sensitivity synchronization thresholds). Optionally, communication subsystem 530 may include hardware configured to perform hardware packet analysis upon event messages 700 in valid communications signals.

Additionally or alternatively, the protocol may utilize dual synchronization thresholds based on assumed bimodal distribution of amplitudes of valid communication in a DC system.

Optionally, programmer 109 may use matching filters instead of a synchronization threshold comparator. For example, LP 102, 104 and programmer 109 may convert all incoming signals to a stream of digital data. In such an embodiment, matching filters compare the stream of digitized data representative of potential candidate device IDs (e.g., in EM preamble field 702) to one or more predetermined reference device IDs. The matching filter may determine that the candidate and predetermined reference device IDs partially or entirely match. When the candidate and reference device IDs partially match, the matching filter also assigns a correlation score indicative of an amount to which the candidate and reference device IDs match. For example, the correlation score may indicate that the candidate and reference device IDs exhibit 50% match, 75% match, 90% match and the like. The processor compares the correlation score to a correlation threshold. When the correlation score exceeds the correlation threshold, the processor declares/ designates the incoming communications signal to represent a valid event message 700 from an authorized device. Alternatively, when the matching filter determines that the candidate and reference codes exhibit an amount of correlation below the correlation threshold, the processor declares/designates the incoming communications signal to be a non-event message and/or from an un-authorized device, such as noise, a communications signal from another source, and the like.

When the device ID is encoded in the EMI preamble and the matching filter is utilized, the synchronization comparator may be omitted as the matching filter correlates the candidate communication signal with one or more valid reference device IDs (also referred to as template IDs). Based on the correlation score, a data threshold may be set and used (as described herein) to decode the remainder of the communication signal.

In accordance with embodiments herein, programmer 109 may be configured to provide communications adjustment information to LPs 102 and 104, where the adjustment information enables LP 102, 104 to better maintain (e.g., optimize) implant-to-implant communication. Programmer 109 is configured to use implant to implant communication to display markers. Programmer 109 is configured to adjust the communications signal, such as to optimize the communication signal sent to the implant (e.g., LP 102, 104).

In some embodiments, the system utilizes dual synchronization thresholds, or synch thresholds, based on digital identification from the implant. The system may also use digital identification that is encoded via data protected marker bits in a "sniff" operation, in which the LP listens over a select transmission channel.

In accordance with embodiments herein, programmer 109 identifies whether one or more than one LP is implanted in the patient without user intervention. Programmer 109 determines the number of LPs based on the number of distinct communications signals received. For example, programmer 109 may identify two or more valid communications signals that convey reference or template synchronization threshold settings/codes, where each communications signal is received at a separate and distinct amplitude. Based on the distribution of amplitudes of valid communication signals, programmer 109 determines the number of LPs. Additionally or alternatively, programmer 109 may determine the number of LPs based on a content of the communications signal. For example, event messages 700 may include an identifier indicating the number of LPs in the patient, the configuration of the LPs (e.g., 1 RA LP and 1 RV LP), and the like.

Additionally or alternatively, programmer 109 may determine the number of LPs based on limits for the atrial ventricular (AV) synchronization times (e.g., based on minimum/maximum AV sync timing). For example, programmer 109 may determine/infer a combination of LPs that operate in a DDD configuration when the programmer identifies markers that are derived from timing configurations that cannot match normal single chamber timing.

The system may adjust implant to implant communication with or without intervention from programmer 109. When using programmer intervention, programmer 109 monitors implant to implant communication to display markers on programmer 109. The event messages may or may not include a device ID. Programmer 109 differentiates the source of event markers based on the low frequency "wakeup" pulse(s). The low frequency wakeup pulses are always included in the event markers. Optionally, the LPs may only include the device ID in event messages only after a programmer session is established.

Optionally, the LP may include high frequency "notches" in the low frequency wakeup pulses, wherein the notches are encoded to differentiate the source LP. Programmer 109 differentiates the LP source of the markers based on the high frequency "notches" in low frequency "wakeup" pulse width. The LP may always include the high frequency notches or alternatively only include the notches after a programmer session is established.

Amplitude based identification may also be used. Amplitude based identification assumes different amplitudes of implants based on orientations/positions relative to programmer electrodes.

In accordance with some embodiments, as noted above, LP 102, 104 and programmer 109 may provide directions instructing LP 102, 104 to adjust (e.g. optimize) the communication signals sent between LP 102, 104 and to/from programmer 109. For example, the communications signals may be adjusted by changing transmit and/or receive signal strengths. As an example, the signal strengths may be adjusted based upon a reciprocity theorem. Namely, for two transceivers operating through the same pair of electrodes: $V_{RX1}/I_{TX2}=V_{RX2}/I_{TX1}$, wherein $V_{RX1}$ represents the receive voltage at a first transceiver (e.g., LP 102), $I_{TX1}$ represents a transmit current at the first transceiver, $I_{TX2}$ represents a transmit current at a second transceiver (e.g., programmer 109), and $V_{RX2}$ represents a receive voltage at the second transceiver. As an example, LP 102 may correspond to the first transceiver, while programmer 109 corresponds to the second transceiver. Programmer 109 ("P") measures a receive signal having a receive voltage amplitude of $V_{RX2}$. Programmer 109 calculates, from the receive voltage amplitude, a transmit current amplitude at LP 102, $I_{TX1}$, based on known transmit impedance. Additionally or alternatively, LP 102 may estimate/determine the LP transmit current, $I_{TX1}$ and communicate the LP transmit current to programmer 109. Once programmer 109 determines the ratio of the LP transmit current and programmer receive voltage (i.e., $V_{RX2}/I_{TX1}$), the same ratio may be applied to determine the programmer transmit current (i.e., $I_{TX2}$) necessary to achieve the same LP receive voltage (i.e., $V_{RX1}$).

Figure 8:
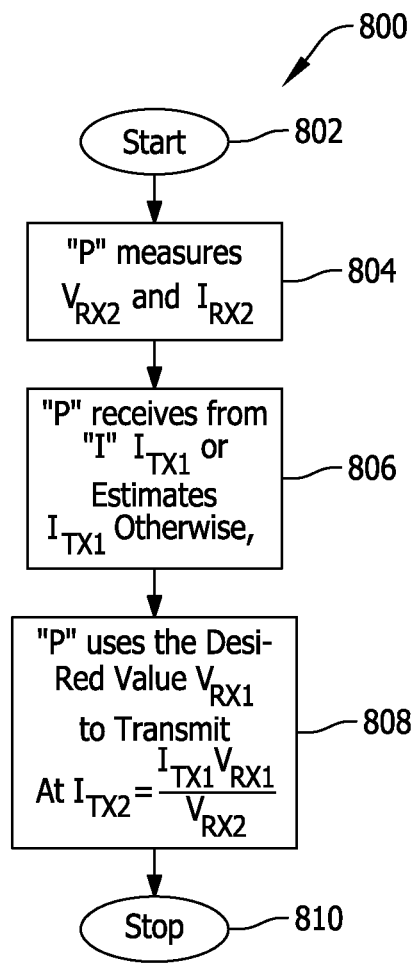
FIG. 8 illustrates a method for changing transmit and/or receive signal strengths in accordance with the embodiments herein.

For example, FIG. 8 is a flowchart of one embodiment of a method 800 for changing transmit and/or receive signal strengths. Method 800 starts at block 802. At block 804, programmer 109 measures $V_{RX2}$ and $I_{TX2}$. At block 806, programmer 109 receives $I_{TX1}$ from LP 102. Alternatively, at block 806, programmer 109 may estimate $I_{TX1}$. At block 808, programmer 109 uses a desired $V_{RX1}$ value to calculate $I_{TX2}$ (i.e., $I_{TX2}=I_{TX1}*V_{RX1}/V_{RX2}$), and transmits at the calculated $I_{TX2}$. Method 800 ends at block 810.

Figure 9:
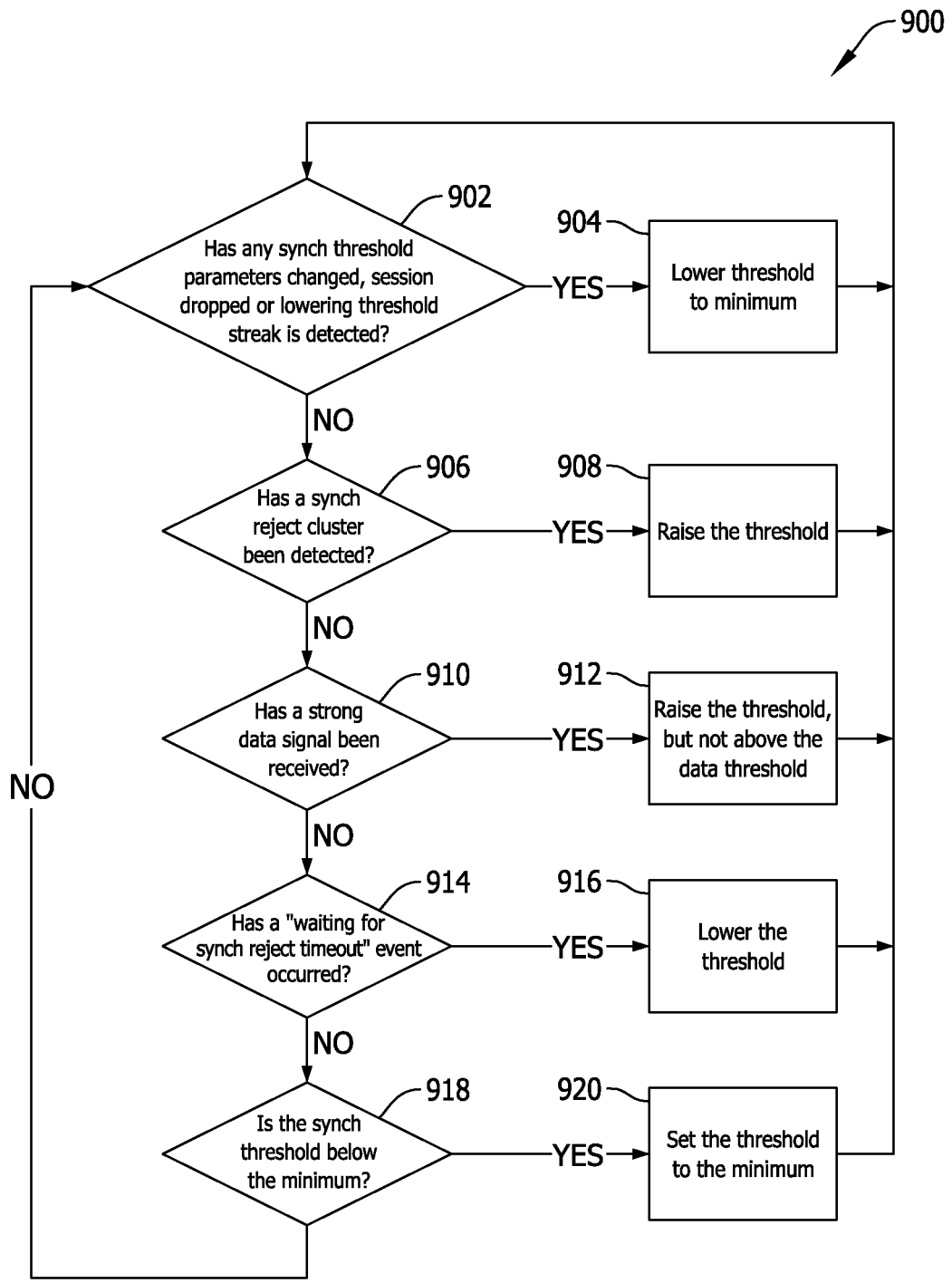
FIG. 9 illustrates a method for managing a synch threshold in accordance with the embodiments herein.

As described above, programmer 109 manages a separate synchronization threshold, or synch threshold, for each LP 102, 104. FIG. 9 is a flowchart of one embodiment of a method 900 for managing a synch threshold. Method 900 is performed by programmer 109 (or programmer 500). For example, method 900 may be used to adjust 606 first and second LP discrimination thresholds in method 600 (shown in FIG. 6). Notably, for a system including two LPs 102 and 104, programmer 109 performs two instances of method 900 in parallel (i.e., one instance for each LP 102, 104).

At block 902, programmer 109 determines whether i) any synch threshold parameters have changed, ii) a programming session has dropped (i.e., ended), or iii) a lowering threshold streak (described below) is detected. If any of these three conditions are satisfied, flow proceeds to block 904, and the synch threshold is lowered to a minimum value. Flow then returns to block 902. If none of the three conditions are satisfied, flow proceeds to block 906.

At block 906, programmer 109 determines whether a synch reject cluster (described below) has been detected. If so, flow proceeds to block 908, and the synch threshold is raised. Flow then returns to block 902. If no synch reject cluster has been detected, flow proceeds to block 910.

At block 910, programmer 109 determines whether a strong data signal (described below) has been received. If so, flow proceeds to block 912, and the synch threshold is raised, but not above a data threshold. Flow then returns to block 902. If no strong data signal has been received, flow proceeds to block 914.

At block 914, programmer 109 determines whether a "waiting for synch reject timeout" event (described below) has occurred. If so, flow proceeds to block 916, where the synch threshold is lowered. Flow then returns to block 902. If no "waiting for synch reject timeout" event has occurred, flow proceeds to block 918.

At block 918, if the synch threshold is currently set below the minimum value, flow proceeds to block 920, and the synch threshold is set to the minimum value. Flow then returns to block 902. If the synch threshold is not currently set below the minimum value, flow returns to block 902.

Figure 10:
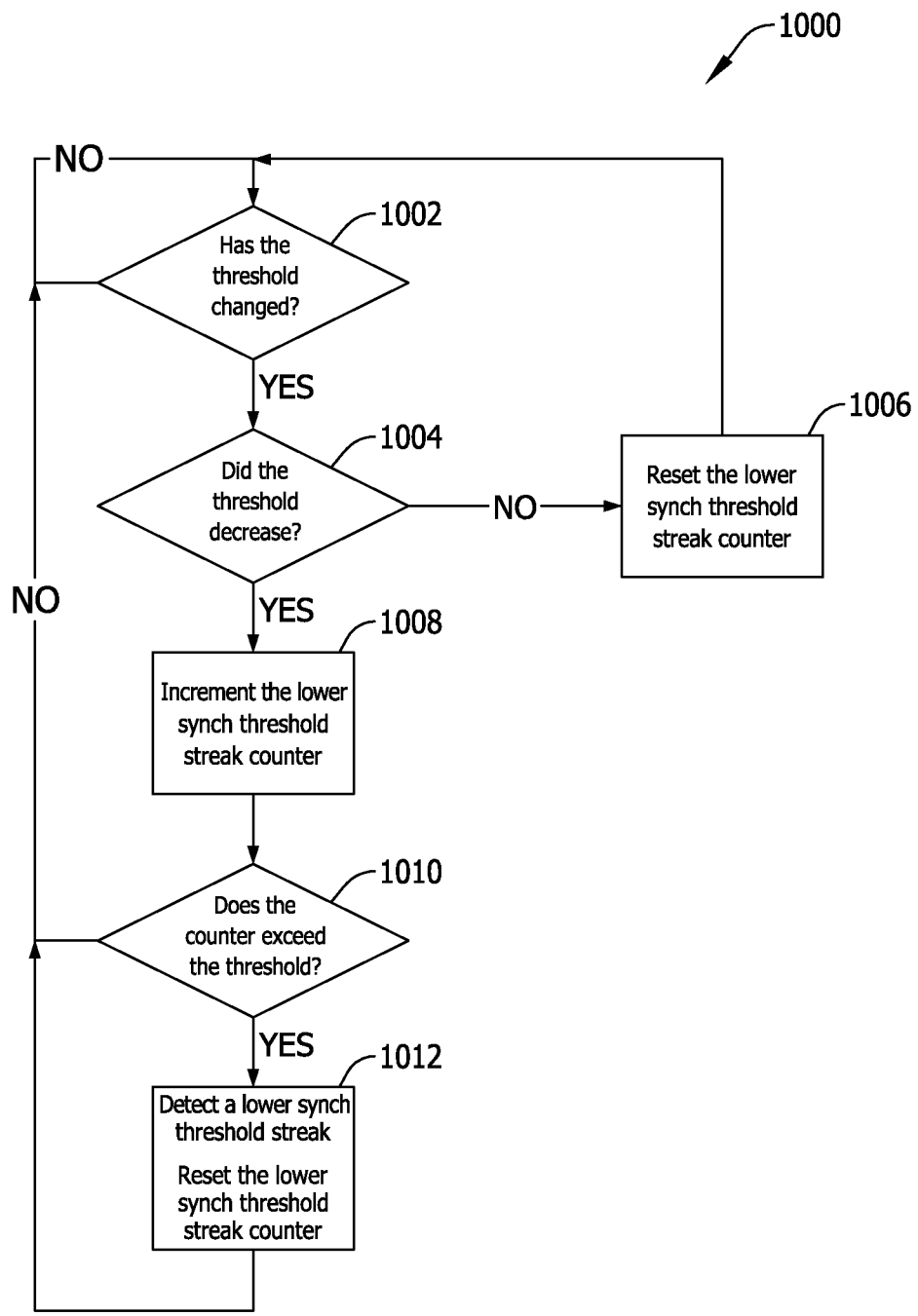
FIG. 10 illustrates a method for detecting a lowering threshold streak in accordance with the embodiments herein.

FIG. 10 is a flowchart of one embodiment of a method 1000 for detecting a lowering threshold streak. For example, method 1000 may be used to implement block 902 (shown in FIG. 9). At block 1002, programmer 109 determines whether the synch threshold has changed. If so, flow proceeds to block 1004. Otherwise, flow simply returns to block 1002.

At block 1004, programmer 109 determines whether the threshold was decreased. If the threshold did not decrease, flow proceeds to block 1006, and a lower synch threshold streak counter is reset. Flow then returns to block 1002. If the threshold did decrease, flow proceeds to block 1008.

At block 1008, programmer 109 increments the lower synch threshold streak counter, and flow then proceeds to block 1010. At block 1010, programmer 109 determines whether the incremented lower synch threshold streak counter exceeds a predetermined threshold (e.g., 5). If not, flow returns to block 1002. However, if the incremented lower synch threshold streak counter does exceed the predetermined threshold, flow proceeds to block 1012.

At block 1012, programmer 109 detects a lowering synch threshold streak, and resets the lower synch threshold streak counter. Flow then returns to block 1002.

Figure 11:
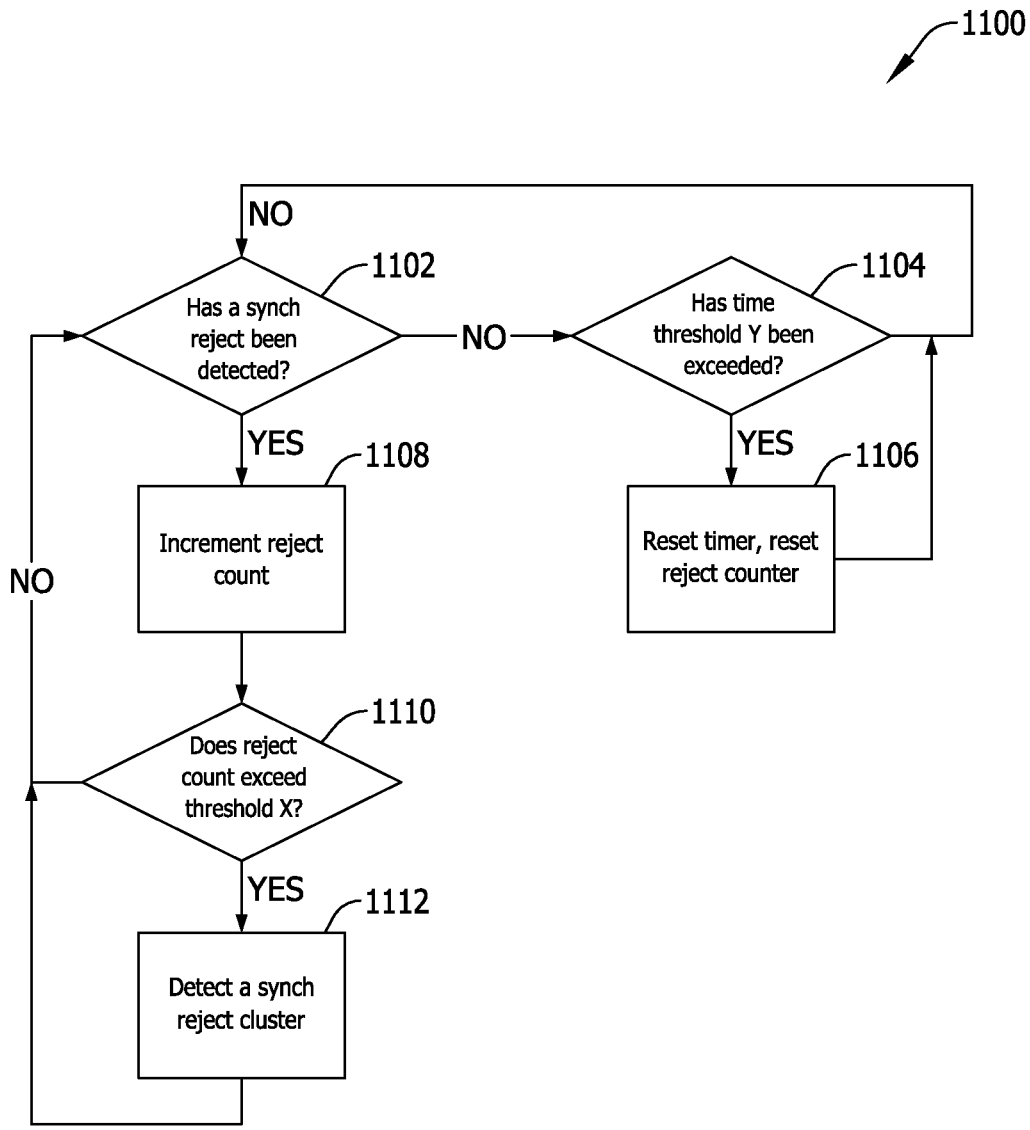
FIG. 11 illustrates a method for detecting a synch reject cluster in accordance with the embodiments herein.

FIG. 11 is a flowchart of one embodiment of a method 1100 for detecting a synch reject cluster. For example, method 1100 may be used to implement block 906 (shown in FIG. 9). At block 1102, programmer 109 determines whether a synch reject has been detected. If a synch reject has not been detected, flow proceeds to block 1104, where programmer 109 determines whether a time threshold, Y, has been exceeded by a running timer.

If the time threshold Y has been exceeded, flow proceeds to block 1106. At block 1106, the timer is reset, a reject count is reset, and flow returns to block 1102. If the time threshold Y has not been exceed, flow returns directly to block 1102.

At block 1102, if a synch reject has been detected, flow proceeds to block 1108, where the reject count is incremented. Flow then proceeds to block 1110, where programmer 109 determines whether the incremented reject count exceeds a reject threshold, X. If the incremented reject count exceeds the reject threshold X, flow proceeds to block 1112, and a synch reject cluster is detected. Otherwise, flow returns to block 1102. Values for time threshold Y and reject threshold X may be stored in a memory of programmer 109, such as RAM 506 (shown in FIG. 5).

Figure 12:
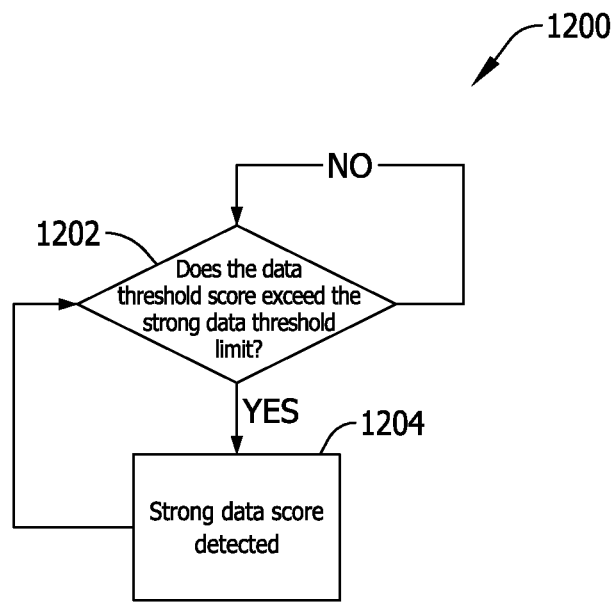
FIG. 12 illustrates a method for detecting a whether a strong data signal has been received in accordance with the embodiments herein.

FIG. 12 is a flowchart of one embodiment of a method 1200 for detecting a whether a strong data signal has been received. For example, method 1200 may be used to implement block 910 (shown in FIG. 9). At block 1202, programmer 109 determines whether a data threshold score of a signal exceeds a predetermined strong data threshold limit. The predetermined strong data threshold limit may be stored in a memory of programmer 109, such as RAM 506 (shown in FIG. 5). If the data threshold score does not exceed the strong data threshold limit, flow simply returns to block 1202. If the data threshold score does exceed the strong data threshold limit, flow proceeds to block 1204, and programmer 109 detects a strong data score, before flow returns to block 1202. In this embodiment, detecting a strong data score corresponds to detecting that a strong data signal has been received.

Figure 13:
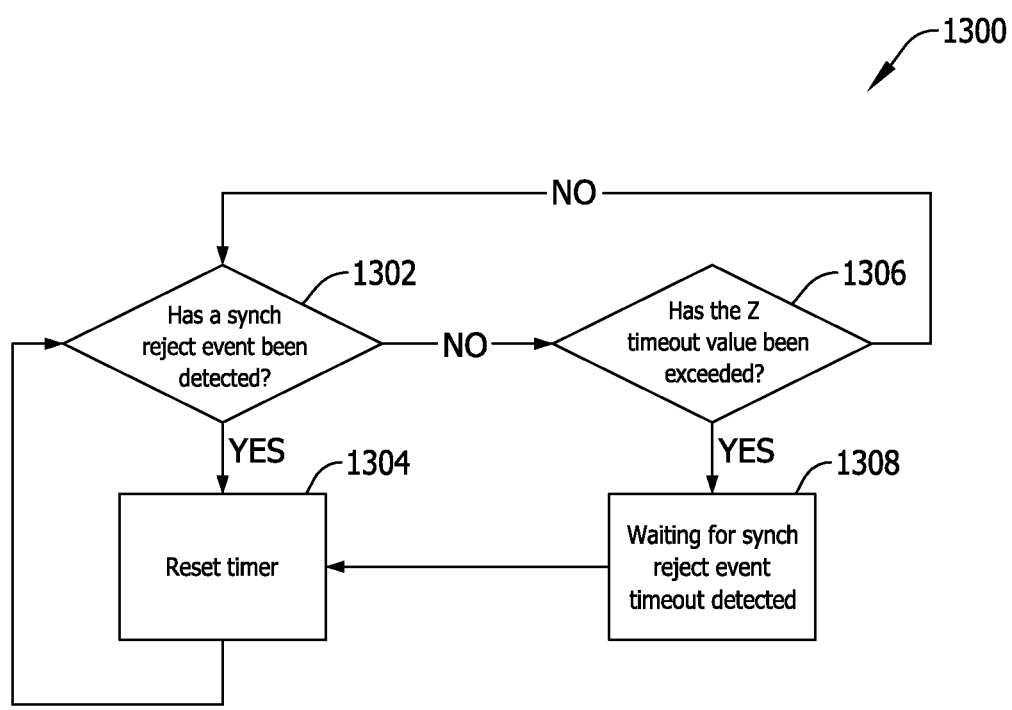
FIG. 13 illustrates a method for determining whether a "waiting for synch reject timeout" event has occurred in accordance with the embodiments herein.

FIG. 13 is a flowchart of one embodiment of a method 1300 for determining whether a "waiting for synch reject timeout" event has occurred. For example, method 1300 may be used to implement block 914 (shown in FIG. 9). At block 1302, programmer 109 determines whether a synch reject event has been detected. If so, flow proceeds to block 1304, and a synch reject timer is reset, before flow returns to block 1302. If, at block 1302, a synch reject event is not detected, flow proceeds to block 1306.

At block 1306, programmer 109 determines whether a timeout value, Z, has been exceeded. Timeout value Z may be stored in a memory of programmer 109, such as RAM 506 (shown in FIG. 5). If the timeout value Z has not been exceeded, flow returns to block 1302. If the timeout value Z has been exceeded, flow proceeds to block 1308. At block 1308, programmer 109 detects a "waiting for synch reject event timeout" event, and flow proceeds to block 1304.

In some embodiments, synch reject clusters and strong data signals are processed only if i) they resulted from a threshold crossing of the current synch threshold and ii) (in the case of strong data signals) decoding of the device ID (i.e., of LP 102, 104) from a higher level indicates that the implant type (i.e., atrial or ventricular) is relevant to the current synch threshold. Further, in some embodiments, if the device ID from the higher level indicates that the implant type is not relevant to the current synch threshold, no modification to the threshold occurs, and the "waiting for synch reject timeout" event is not reset.

In some embodiments, programmer 109 and/or LP 102, 104 may utilize additional electrode configurations to provide conducted communication. Electrode diversity leads to increased signal amplitude and decreased noise for communication to each implant. The additional transmit/receive vectors may assist in estimating the relative position and orientation of the implants based on received communication amplitudes at the different programmer electrodes. This could be helpful to the user during the implantation process and guide implant placement for more optimal implant to implant communication.

The module/controller may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the (module/controller) represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The (module/controller) may execute a set of instructions that are stored in one or more storage elements, in order to process data. The storage elements may also store data or other information as desired or needed. The storage element may be in the form of an information source or a physical memory element within the (module/controller). The set of instructions may include various commands that instruct the (module/controller) to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method for providing communications between an external device and first and second leadless pacemakers (LPs) located in a heart, the method comprising:
   receiving first and second event messages from the first and second LPs, the first and second event messages received at different points in time at the external device;
   determining the signal strengths of the first and second event messages, respectively, as received at the external device;
   adjusting first and second LP discrimination thresholds based on the received signal strengths of the first and second event messages, respectively; and
   using the external device to independently communicate with the first and second LPs utilizing the first and second LP discrimination thresholds to identify which of the first and second LP transmits subsequent event messages.

2. The method of claim 1, further comprising:
   measuring a receive voltage of the external device;
   determining a transmit current of the first LP;
   calculating a transmit current of the external device based on the receive voltage of the external device, the transmit current of the first LP, and a desired receive voltage of the first LP; and
   transmitting a signal from the external device to the first LP at the calculated external device transmit current.

3. The method of claim 1, wherein adjusting the first and second LP discrimination thresholds comprises:
   determining, for the first discrimination threshold, i) whether any synch threshold parameters have changed, ii) whether a programming session has ended, and iii) whether a lowering threshold streak is detected; and lowering the discrimination threshold to a predetermined minimum value when at least one of i) any synch threshold parameters have changed, ii) the programming session has ended, and iii) the lowering threshold streak is detected.

4. The method of claim 3, further comprising:
incrementing a lower synch threshold streak counter when the first discrimination threshold is decreased;
comparing the incremented lower synch threshold streak counter to a predetermined threshold; and
detecting the lowering threshold streak when the incremented lower synch threshold streak counter exceeds the predetermined threshold.

5. The method of claim 1, wherein adjusting the first and second LP discrimination thresholds comprises:
detecting, for the first discrimination threshold, a synch reject cluster; and
increasing the first discrimination threshold in response to the detected synch reject cluster.

6. The method of claim 5, wherein detecting a synch reject cluster comprises:
detecting a sync reject;
incrementing a reject counter in response to the detection;
comparing the incremented reject counter to a predetermined threshold; and
detecting the synch reject cluster when the incremented reject counter exceeds the predetermined threshold.

7. A programmer for use in a cardiac stimulation system, the programmer comprising:
a memory device; and
a processor coupled to the memory device, the processor configured to:
receive first and second event messages from first and second leadless pacemakers (LPs) located in a heart, the first and second event messages received at different points in time at the programmer;
determine the signal strengths of the first and second event messages, respectively, as received at the programmer;
adjust first and second LP discrimination thresholds based on the received signal strengths of the first and second event messages, respectively; and
utilize the first and second LP discrimination thresholds to identify which of the first and second LP transmits subsequent event messages, in order for the programmer to independently communicate with the first and second LPs.

8. The programmer of claim 7, wherein the processor is further configured to:
measure a receive voltage of the programmer;
determine a transmit current of the first LP;
calculate a transmit current of the programmer based on the receive voltage of the programmer, the transmit current of the first LP, and a desired receive voltage of the first LP; and
transmit a signal from the programmer to the first LP at the calculated programmer transmit current.

9. The programmer of claim 7, wherein to adjust the first and second LP discrimination thresholds, the processor is configured to:
determine, for the first discrimination threshold, i) whether any synch threshold parameters have changed, ii) whether a programming session has ended, and iii) whether a lowering threshold streak is detected; and
lower the discrimination threshold to a predetermined minimum value when at least one of i) any synch threshold parameters have changed, ii) the programming session has ended, and iii) the lowering threshold streak is detected.

10. The programmer of claim 8, wherein the processor is further configured to:
increment a lower synch threshold streak counter when the first discrimination threshold is decreased;
compare the incremented lower synch threshold streak counter to a predetermined threshold; and
detect the lowering threshold streak when the incremented lower synch threshold streak counter exceeds the predetermined threshold.

11. The programmer of claim 7, wherein to adjust the first and second LP discrimination thresholds, the processor is configured to:
detect, for the first discrimination threshold, a synch reject cluster; and
increase the first discrimination threshold in response to the detected synch reject cluster.

12. The programmer of claim 11, wherein to detect a synch reject cluster, the processor is configured to:
detect a sync reject;
increment a reject counter in response to the detection;
compare the incremented reject counter to a predetermined threshold; and
detect the synch reject cluster when the incremented reject counter exceeds the predetermined threshold.

13. A system for applying cardiac stimulation to a patient, the system comprising:
a first leadless pacemaker (LP) implanted in a first chamber of a heart of the patient;
a second LP implanted in a second chamber of the heart; and
a programmer configured to:
receive first and second event messages from the first and second LPs, the first and second event messages received at different points in time at the programmer;
determine the signal strengths of the first and second event messages, respectively, as received at the programmer;
adjust first and second LP discrimination thresholds based on the received signal strengths of the first and second event messages, respectively; and
independently communicate with the first and second LPs utilizing the first and second LP discrimination thresholds to identify which of the first and second LP transmits subsequent event messages.

14. The system of claim 13, wherein the first LP is implanted in an atrial chamber of the heart, and wherein the second LP is implanted in a ventricular chamber of the heart.

15. The system of claim 13, wherein the programmer is further configured to:
measure a receive voltage of the programmer;
determine a transmit current of the first LP;
calculate a transmit current of the programmer based on the receive voltage of the programmer, the transmit current of the first LP, and a desired receive voltage of the first LP; and
transmit a signal from the programmer to the first LP at the calculated programmer transmit current.

16. The system of claim 13, wherein to adjust the first and second LP discrimination thresholds, the programmer is configured to:
determine, for the first discrimination threshold, i) whether any synch threshold parameters have changed, ii) whether a programming session has ended, and iii) whether a lowering threshold streak is detected; and lower the discrimination threshold to a predetermined minimum value when at least one of i) any synch threshold parameters have changed, ii) the programming session has ended, and iii) the lowering threshold streak is detected.

17. The system of claim 13, wherein to adjust the first and second LP discrimination thresholds, the programmer is configured to:

detect, for the first discrimination threshold, a synch reject cluster; and increase the first discrimination threshold in response to the detected synch reject cluster.

* * * * *